United States Patent [19]

Foxwell et al.

[11] Patent Number: 5,459,240
[45] Date of Patent: Oct. 17, 1995

[54] PEPTIDES WHICH SERVE AS SUBSTRATES FOR A PHOSPHOKINASE AND METHODS FOR THEIR USE TO MODIFY ANTIBODIES IN ORDER TO FACILITATE RADIOABELLING OF ANTIBODIES WITH $^{32}$P

[76] Inventors: Brian M. J. Foxwell, 28, Cassell House, Stockwell, London, SW9 9AY; Peter Parker, 42A The Parade Epsom, Surrey KT18 5DU; Andrew M. Creighton, 68, Millway, Mill Hill, London, NW7 3QY, all of England

[21] Appl. No.: 320,125

[22] Filed: Oct. 7, 1994

Related U.S. Application Data

[63] Continuation of Ser. No. 617,916, Nov. 21, 1990, abandoned, which is a continuation of Ser. No. 37,313, Apr. 13, 1987, abandoned.

[51] Int. Cl.$^6$ ............................. C07K 7/06; C07K 16/46
[52] U.S. Cl. ....................... 530/328; 530/345; 530/402; 530/391.1
[58] Field of Search ................................. 530/328, 329, 530/331, 345, 350, 391.1, 391.3, 391.5, 391.9, 402; 435/262, 194, 17

[56] References Cited

U.S. PATENT DOCUMENTS

| | | | |
|---|---|---|---|
| 4,318,904 | 3/1982 | Shaw et al. | 514/18 |
| 4,745,055 | 5/1988 | Schenk et al. | 435/7.6 |

OTHER PUBLICATIONS

Goldenberg, CA Cancer J. Clin. 44:43–64,1994.
Harris et al. Tibtech 11:42–44, 1993.
Osband et al. Immunology Today 11(6):193–195, 1990.
Band et al., *Imperial Cancer Research Fund Annual Report* (1987) p. 148, section 45.1.
Foxwell et al., *Imperial Cancer Research Fund Annual Report* (1986) p. 157, section 37.6.
Foxwell et al., *British J. Cancer* (1986) 54:536.
O'Brian et al., (1984) Biochem. Biophys. Res. Comm. 124(1):296–302.
Feramisco et al., (1978) Journal of Biological Chemistry 253(24):8968–8971.
Kemp et al., (1986) Fed. Proc. 35, 1384, abstract No. 139.
Maller et al., (1978) Proc. Natl. Acad. Sci. USA 75(1):248–251.

*Primary Examiner*—Paula K. Hutzell
*Attorney, Agent, or Firm*—Morrison & Foerster

[57] ABSTRACT

A method is provided for attaching $^{32}$P to a protein, normally an antibody, that will bind with and irradiate a tumor-associated structure leading to diagnostic benefit. The invention is based upon the introduction of a peptide region to the protein, which is capable of acting as a substrate for a phosphokinase utilizing $^{32}$P-γ-ATP as a typical source of the radionuclide. The conjugation of the substrate molecule to the protein may be achieved by chemical methods or by genetic engineering techniques. Novel substrate peptides are disclosed.

6 Claims, 2 Drawing Sheets

PEPTIDES WHICH SERVE AS SUBSTRATES FOR A PHOSPHOKINASE AND METHODS FOR THEIR USE TO MODIFY ANTIBODIES IN ORDER TO FACILITATE RADIOABELLING OF ANTIBODIES WITH $^{32}P$

This application is a continuation of application Ser. No. Ser. No. 07/617,916, filed Nov. 21, 1990 abandoned which is a continuation of Ser. No. 07/037,313 filed Apr. 13, 1987, abandoned.

BACKGROUND OF THE INVENTION

This invention relates to the radio-labelling of proteins and is specifically concerned with the labelling of monoclonal antibodies and other proteins with $^{32}P$. The term "protein" as used herein encompasses polypeptides.

The concept of using monoclonal antibodies, and other proteins as delivery vehicles for the targeting of drugs is already established. Practical difficulties exist however when it comes to attaching the drug to the monoclonal antibody or other delivery system since this must be done in such a way that the activity of the drug is retained and, at the same time, the specificity of the monoclonal antibody or other delivery system is maintained. At a practical level, this places considerable restriction upon those chemical and biological methods theoretically available for the linking of the drug to the delivery system as many conventional reaction conditions will destroy either or both of the drug activity and delivery system specificity.

Radiation therapy is now well-established as one possible method of treatment of certain cancer conditions and the attachment of the radio-isotopes of iodine and a variety of metals, e.g. indium and yttrium to antibodies is currently being investigated for this purpose. The radionuclide $^{32}P$ is, in many ways, a particularly advantageous radionuclide for use against certain types of solid tumours with relatively poor blood supply since $^{32}P$ has a reasonably short half-life of 14 days and it is a pure beta-emitter with a particle energy of 1.7 MeV. However, it has not been possible to attach $^{32}P$ to antibodies by the methods that have been used previously for the attachment of other radio-isotopes.

STATEMENT OF THE INVENTION

We have now found a method by which a monoclonal antibody or similar targeting molecule can be structurally modified so that it can readily and swiftly have attached to it $^{32}P$ under mild reaction conditions that maintain the specificity of the targeting molecule so as to give a $^{32}P$ labelled material.

The present invention provides a method for modifying a protein that will bind with a tumour-associated structure such as protein, glycolipid or carbohydrate, comprising the introduction into the binding protein of a peptide region, which is capable of acting as a substrate for a phosphokinase. The resulting modified binding protein can then be $^{32}P$ labelled by reacting it with a 32P-labelled gamma nucleotide triphosphate in the presence of a phosphokinase.

This method gives rise to a binding protein (targeting molecule) carrying a $^{32}P$ label. Such $^{32}P$ labelled compounds are new and form a further aspect of the present invention.

The binding protein will normally be a monoclonal antibody that will bind with a tumour-associated antigen, for example antigens associated with solid tumours with relatively poor blood supplies. Such solid tumours include those found in the colon, ovaries and lungs and monoclonal antibodies to such tumour-associated antigens are already known and have already been used as delivery vehicles for other anti-tumout agents. Such known antibodies can be linked to $^{32}P$ by the techniques of the present invention.

More generally, the binding protein may be any protein that will bind with tumour-associated protein (or other tumour-associated structure such as a glycolipid or carbohydrate) where the tumour is one susceptible to high-energy beta particles and, in addition to monoclonal antibodies, the first protein could be, for example, an Fab fragment or a hormone or similar peptide that will bind to an appropriate receptor site identified on certain types of tumour cell e.g. melanocyte-stimulating hormone, epithelial growth factor, interferons and mitogenic peptides such as bombesin.

BRIEF DESCRIPTION OF THE DRAWINGS

This invention will be described with reference to the drawings in which.

DETAILED DESCRIPTION OF THE INVENTION

Figure 1:
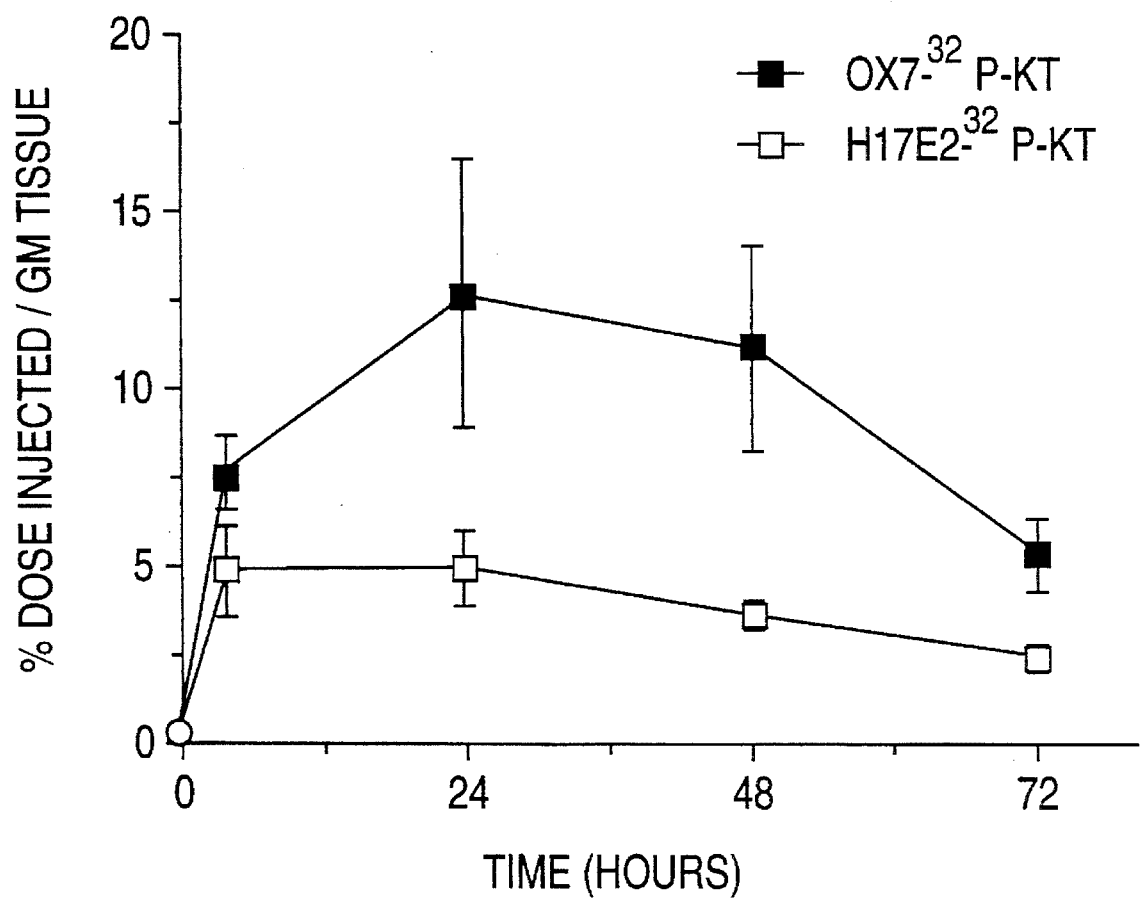
FIG. 1 is a graph illustrating accumulation of radio-labelled Kemptide conjugates in tumors as a function of time.

The present invention is based upon the structural modification of the binding protein to introduce a peptide region capable of acting as a substrate for the phosphokinase so that when the structurally modified "binding protein" which can be regarded as a "protein"/substrate conjugate is brought into contact with the $^{32}P$ containing phosphorylating agent in the presence of a phosphokinase, the enzyme can catalyse the transfer of $^{32}P$ from the phosphorylating agent into the substrate region of the conjugate.

Present availability points to the use of serine/threonine kinases as the phosphokinase. Such materials are now commercially available from the Sigma Company e.g. bovine heart protein kinase.

A hepta peptide known as Kemptide and having the structure Leu.Arg.Arg.Ala.Ser.Leu.Gly is now commercially available and is known to be a satisfactory substrate for the bovine heart protein kinase where phosphorylation with gamma-$^{32}P$-adenosine triphosphate (ATP) results in $^{32}P$ phosphorylation at the serine residue of Kemptide. We have now surprisingly found that if the Kemptide structure is grafted onto a monoclonal antibody, not only is the specificity of the monoclonal antibody unaffected but also that the ability of the monoclonal antibody/Kemptide conjugate to act as a substrate for the kinase is unimpaired and that phosphorylation from gammas-$^{32}P$-ATP can still proceed in a similar way to phosphorylation of the heptapeptide molecule itself.

One practical benefit of our new technique is that the monoclonal antibody or other protein can be partially prepared for phosphorylation by conjugation with the heptapeptide and the phosphorylation left until immediately before the radio-labelled molecule is to be administered to the patient.

The concept of the present invention does not depend upon the use of the specific heptapeptide Kemptide and indeed, any peptide can be use provided it is capable of acting as a substrate for the phosphokinase. If the phosphokinase is the serine/threonine kinase derived from bovine heart as described in Example 4, then the main structural requirement for the substrate molecule appears to be that there be an area of positive charge, e.g. arising from arginine and/or lysine residues, close to the serine and/or threonine residues in the substrate. Kemptide is one such substrate but we have worked with other similar molecules in which we have replaced the leucine residue at the N-terminus of Kemptide by a lysine-tyrosine dipeptide to give an octapeptide Lys.Tyr.Arg.Arg.Ala.Ser.Leu.Gly we have called Foxtide I. The advantages of Foxtide I over Kemptide are that conjugating the substrate molecule to the antibody molecule is facilitated by the existence of the lysine residue at the N-terminus while the presence of the tyrosine molecule gives ultra-violet "visibility" to the substrate molecule facilitating purification and identification.

We have also developed another substrate molecule meeting the general requirements set out above but which is a decapeptide of the structure: Cys.Arg.Arg.Lys.Ala. Ser.Gly. Pro. Pro.Val. We have designated this decapeptide Foxtide II. Foxtide II has advantages over Kemptide for our purposes in that the serine residue can be phosphorylated more quickly than can the serine residue in Kemptide under otherwise similar reaction conditions using gamma-$^{32}$P-ATP in the presence of bovine heart protein kinase. Additionally, the cysteine residue at the N-terminus facilitates conjugation with the monoclonal antibody or other first protein through the SH grouping in the terminal residue. Foxtide I and Foxtide II may be prepared by conventional solid state peptide synthesis on a Merrifield resin.

Foxtide I and Foxtide II are new compounds and these new compounds form part of the present invention.

The substrate molecules discussed so far are all substrates for serine/threonine kinases but other types of phosphokinases are known and can be used with the appropriate substrate. For example, phosphokinases which are tyrosine kinases are known and substrates for such tyrosine kinases are known in which the enzyme brings about phosphorylation of the tyrosine residue. Examples of such tyrosine kinases include these contained in Lymphoma cell extracts as described by Casnellie et al, PNAS, 1982, 79, 282–6. An example of a substrate for the tyrosine kinases:

Ile-Glu-Asp-Asn-Glu-Tyr-Thr-Ala-Arg-Gln-Gly.

The kinase substrates used in the present invention can be of any molecular size. The tendency is to use a substrate which is as small as possible since the only requirement is to have a phosphorylatable residue, e.g. serine, threonine or tyrosine which, depending upon the enzyme being used, may need to be in a close relationship to the area of positive charge. Practicalities such as the cost of synthesis and ease of purification will therefore point to the use of small peptides containing up to about 20 amino acid residues but larger substrates could be used, bearing in mind that the larger the substrate the more likely it is to interfere with the properties of the final first protein/substrate conjugate.

Chemical methods can be used for the conjugation of the substrate molecule to the monoclonal antibody or other binding protein. Essentially, it is necessary to bring about activation to an appropriate level of reactive groupings in the first protein and in the substrate molecule so that the necessary bonds can be formed so as to bring about conjugation while, at the same time, avoiding the use of reaction conditions that will cause modification of the specificity of the first protein in relation to the tumour associated protein and the capacity of the substrate molecule to act as a substrate during the subsequent phosphokinase phosphorylation.

We have found that satisfactory linking of the substrate molecule to the targeting molecule (the binding protein) can be achieved using appropriate hetero-bifunctional protein crosslinking agents. For example, the targeting molecule may be reacted with N-succinimidyl-3-(2-pyridyldithio)propionate (SPDP) followed by reduction with dithiothreitol. The reaction with SPDP introduces the dithiopropionyl group onto a side-chain amino group of a lysine residue in the targeting molecule while the subsequent reduction step converts the dithio grouping into a terminal thiol group. This terminal thiol group provides the reactive site for introduction of the substrate molecule.

The substrate molecule can be activated for conjugation to the targeting molecule for example by reacting the alpha-amino group of the terminal leucine residue of Kemptide with the corresponding N-hydroxysuccinimidyl esters to give for example an iodoacetamide or a phenyl maleimide which can then react with the thiol group of the thiopropionamido residue introduced on the targeting molecule so that the substrate molecule becomes attached to the targeting molecule through a short bridging group including a thio link.

For conjugation with a substrate molecule which has a reactive thiol group, such as Foxtide II, the first protein may be activated by reacting it with e.g. SMPB [succinimidyl-4-(p-maleimidophenyl)butyrate]. Other reagents that can be used for this purpose include MBS (m-maleimidobenzoyl-N-hydroxy succinimide ester), SMCC [succinimidyl-4-(N-maleimidomethyl)-cyclohexane-1 -carboxylate] and SIAB [N-succinimidyl-(4-iodoacetyl)aminobenzoate], all of which are commercially available.

The conjugates formed by linking the first protein (i.e. the targeting molecule) to the substrate molecule through a bridging group originating from the heterobifunctional crosslinking agent are themselves new compounds and form a further aspect of the present invention. In addition to the conventional synthetic methods described above for producing the protein/substrate conjugate, the appropriate substrate sequence may be integrated into an appropriate position within the primary structure of the first protein by using genetic engineering techniques and the use of such techniques is also within the scope of this invention.

The targeting molecule/substrate molecule conjugates are stable materials that can be stored for prolonged periods of time at room temperature or slightly below, e.g. 0° to 20° C. We have found that, after conjugation of the targeting molecule with the substrate molecule using hetero-bifunctional protein crosslinking agents, the specificity of the targeting molecule and the substrate capacity of the substrate molecule is retained both initially and after prolonged storage at 0° to 20° C.

One of the benefits of the present invention is that the targeting molecule/substrate molecule conjugate can be stored in this form for prolonged periods of time prior to use and that it can be easily phosphorylated to introduce the $^{32}$P function immediately prior to use in a patient. The phosphorylation itself can be carried out by any conventional phosphokinase/phosphorylating agent system and we have found that satisfactory results can be readily achieved e.g. in periods of about 30 minutes, using $^{32}$P gamma-ATP (e.g. the material sold as product Code PB10218 by Amersham International Limited, England) with bovine heart protein kinase and a phosphorylatable serine or threonine residue in the substrate portion of the conjugate. As an alternative to $^{32}$ P-gamma-ATP, one can also use 32P-gamma-guanidine triphosphate as phosphorylating agent used in association with the appropriate phosphokinase. These phosphorylating agents may also be used in association with the appropriate phosphokinases to introduce $^{32}$P onto the tyrosine residue in conjugates having a tyrosine residue in the substrate portion.

Although the present invention is primarily designed to facilitate enzymatic phosphorylation of the phosphorylatable amino acid residues in the substrate portion of the conjugate, chemical phosphorylation would also be possible.

Once the phosphorylation of the targeting molecule/substrate molecule conjugate has been completed, the $^{32}$P labelled material can be purified from inorganic materials by standard chromatographic techniques such as gel filtration, e.g. on a Sephadex column equilibrated with phosphate buffered saline. The $^{32}$P conjugate solution obtained in this way may then be filtered (0.22 µ) and is then in a suitable form for administration.

According to a further feature of the invention, we provide a pharmaceutical composition, particularly one for parenteral administration, comprising a pharmaceutically acceptable diluent, and a $^{32}$P-labelled protein that will bind with a tumour-associated structure.

Once a trace dose of radiolabelled binding protein is shown to target preferentially for a tumour as compared to normal tissue, then the 32P-labelled binding protein may be given to the subject intravenously or into various body regions e.g. by intraperitoneal, intrapleural or intra-arterial infusion.

The use of the 32P-labelled binding protein according to the invention has the advantage that the procedures for protection during handling and preparing the radioactive products are simplified, external radiation doses to staff are reduced and storage and disposal problems are simplified by the non-volatile nature of the material. $^{32}$P has advantages over other radioactive isotopes, for example $^{131}$I, in that a patient can receive a higher dose rate with $^{32}$P-labelled binding protein since the relative activity concentration required to deliver a specific dose to a target is less than that required for $^{131}$I; the unit dose delivered to a particular target tissue using phosphorus-labelled targeting molecules is, for example, approximately twice that delivered when using $^{131}$I labelled targeting molecules. Moreover the effects of this radiation therapy on uninvolved tissues are reduced significantly by the absence of penetrating gamma radiation.

Damage to uninvolved tissues may be minimised by administration of $^{31}$P-orthophosphate salts for a period of several weeks following treatment with the $^{32}$P-labelled binding protein.

The most sensitive normal tissue is. the bone marrow and the application of marrow transplantation is also within the scope of this invention to allow the use of very high doses of 32P-labelled binding protein.

The $^{32}$P-labelled binding proteins are of interest in the treatment of, for example, ovarian cancer, colon metastases to the liver, malignant pleural effusions and brain tumours.

The following Examples are given to illustrate the way in which the invention can be put into practice using, as targeting molecules, monoclonal antibodies that will bind to solid tumours implanted in mice.

EXAMPLE 1

Introduction of an iodoacetyl group into the peptide receptor molecule "Kemptide" (Leu.Arg.Arg.AlaSer.Leu.Gly).

N-Succinimidyl-2-iodoacetate (0.75 mg, 2 eq.) in dry dimethyl formamide (DMF, 62.5 µl) was added to a solution of "Kemptide" (1.5 mg) in water (60 µl ) which had first been diluted with methanol (40 µl ). After incubation for one hour at room temperature, the reaction was shown to be complete by analysis of a sample with thin layer chromatography (TLC) (6065 Cellulose plates, Eastman, eluting with 1-butanol: water: acetic acid: pyridine in the proportions 50: 40: 2: 32 v/v) - ninhydrin staining demonstrated the removal of the free primary amino groups. The reaction mixture was then used directly for coupling to the thiopropylated antibody as described in Example 2.

EXAMPLE 2

Introduction of a thio group into OX7 antibody and subsequent coupling with iodacetyl "Kemptide".

A solution of N-succinimidyl-3- (2-pyridyldithio)propionate (SPDP) (44 µl of a stock solution of 3.1 mg/ml in dry DMF) was added to a solution of OX7 monoclonal antibody (7.8 mg) in borate buffer (1.0 ml, 0.05M sodium borate containing 0.1M sodium chloride and 0.5% v/v 1-butanol; pH 9.0). The molar ratio of SPDP to immunoglobulin was 8:1. After incubation at room temperature for one hour, the reaction mixture was desalted on a G50 'Sephadex' column (60 ml) which had been equilibrated in acetate buffer (0.1M sodium acetate containing 0.1 M sodium chloride and 1 mM ethylene diamine tetraacetic acid (EDTA); pH 4.5). Analysis of the eluted protein by the standard method of Carlsson et al., (Biochem J. 1978, 173, 723) revealed that an average of 4.6 dithiopropyl groups had been introduced per IgG molecule. The protein solution (5.6 ml) was then incubated with dithiothreitol (275 µl of molar stock solution to give a final concentration of 50 mM) for one hour at room temperature and then desalted on a G50 'Sephadex' column (60 ml) equilibrated in nitrogen-flushed phosphate buffer (0.1M disodium hydrogen phosphate buffer (pH 7.5) containing 0.1M sodium chloride and 1 mM EDTA). The eluted protein was immediately concentrated again by 'Amicon' ultrafiltration to 1.0 ml, 6.3 mg/ml), diluted with DMF (200 µl) and treated with the iodacetylated Kemptide solution (30 µl, prepared as described in Example 1). This gave a final ratio of 2.5 iodoacetyl residues per thiopropyl group. The reaction mixture was incubated at room temperature for 24 hours and any remaining unreacted thiol groups were then blocked by the addition of a solution of N-ethylmaleimide (5 rag) in DMF (100 £1). After a further hour, the reaction mixture was applied to a G50 'Sephadex' column (60 ml) equilibrated in the "enzyme buffer" (50 mM potassium hydrogen phosphate (pH 7.0) containing 5 mM magnesium chloride and 0.25 mM EGTA [ethyleneglycol-bis- (beta-aminoethyl ether) -N,N,N$^1$ ,N$^{1-}$-tetraacetic acid]) and the eluted protein concentrated to 1 mg/ml by 'Amicon' ultrafiltration, filtered (0.22µ) and stored at 4° C. The number of 'Kemptide' groups conjugated to each antibody molecule by this procedure was shown to be about 2.0 by trace-labelling a sample of the product with $^{32}$P.

EXAMPLE 3

Retention of antibody function by OX7-'Kemptide' conjugate Solutions of OX7-Kemptide conjugate (50 ul, prepared as described in Example 2) at various concentrations were added to aliquots of AKR-A mouse lymphoma cells (1 ml at 10$^6$ cells/ml) in phosphate buffered saline (PBS) containing bovine serum albumen (BSA) (2 mg/ml) and sodium azide (0.05%). After incubation at 37° C. for 30 minutes, the cells were washed twice with the PBS solution and the resultant cell pellets treated with fluorescein isothiocyanate-labelled rabbit anti-mouse antibody (Miles Labs.), diluted 1:32 from stock. After incubation for 30 minutes at 37° C., the cells were washed in PBS/BSA/azide solution and finally suspended in 1 ml of the buffer solution. Flow cytometry analysis of at least $10^4$ cells at each concentration showed that conjugate and native OX7 had identical binding characteristics and there was no evidence of a decrease in affinity of the conjugated OX7. 50% saturation of the binding sites was achieved at about 60 ng/ml of OX7 or OX7-'Kemptide'.

EXAMPLE 4

Phosphorylation of OX7-'Kemptide'

For high specific activity labelling, OX7-'Kemptide' stock solution (70 µl at 1 mg/ml, prepared as described in Example 2) and ×5 "enzyme buffer" (30 µl, 250 mM dipotassium hydrogen phosphate (pH 7.0) containing 25 mM magnesium chloride and 1.25 mM EGTA) was added to 1 mCi of 32P-y-ATP (adenosine triphosphate) (100 µl, PB10218, Amersham International), followed by bovine heart protein kinase (5 µl,50 U, Sigma). The reaction was incubated for 30 minutes at 37° C. and the protein was then desalted using a G50 'Sephadex' column (10 ml) equilibrated in phosphate-buffered saline which had been prewashed in phosphate-buffered saline containing bovine serum albumin (2 mg/ml). Under these conditions, about 0.15 phosphate moieties were incorporated into each molecule of OX7 with a specific activity of 5.26 µCi/ug.

EXAMPLE 5

Preparation of a conjugate from iodoacetyl 'Kemptide' and H17E2

H17E2 is a monoclonal antibody raised against alpha-placental alkaline phosphatase which is normally found in placenta but is also expressed by ovarian, testicular, cervical and glioma tumour tissue. This conjugate was prepared in essentially the same way as Example 2 but using H17E2 (10 mg), SPDP (170 µg) dithiothreitol (65 µl of molar solution) and iodoacetyl-'Kemptide' (67µl of the solution, prepared as described in Example 1). Seven thiol groups were introduced to the antibody by this procedure and a three-fold excess of iodoacetyl-Kemptide was used to maximise coupling. Any remaining unreacted thiol was then blocked with N-ethylmaleimide (6 rag) in DMF (120µl). Labelling with trace amounts of $^{32}$P showed that there was an average of about 4.52 sites on each antibody molecule that could be labelled with $^{32}$P. Labelling at high-specific activity as described in Example 4 gave a product with a specific activity of 5.23 µCi/ug.

EXAMPLE 6

Preparation of a conjugate from iodoacetyl 'Foxtide' and the monoclonal antibody OX7

N-Succinimidyl-2-iodoacetate (0.28 rag, 1 eq) in dry DMF (14µl) was added to a solution of 'Foxtide I' (Lys.Tyr.Arg.Arg.Ala.Ser.Leu.Gly) (1 rag) in water (40 µl) diluted with methanol (60 µl) which was then treated with 100 µM sodium hydroxide (14 µl ) giving a pH of 6.4. After incubation for one hour at room temperature, TLC followed by ninhydrin staining indicated that the reaction was complete. A sample of this reaction mixture (60 µl) was added to a solution of thiolated OX7 monoclonal antibody (650 µl, prepared as described in Example 2) and incubated at 4° C. for 72 hours. Unreacted thiol groups (if any) were then blocked by the addition of N-ethylmaleimide (5 rag) in DMF (50 µl) and after incubation for one hour,the conjugate was isolated and stored in the enzyme buffer as described in Example 2. The number of Foxtide I groups conjugated to each antibody molecule by this procedure was shown to be 1.32 by trace-labelling a sample of the product with $^{32}$P.

EXAMPLE 7

Stability of phosphorylated conjugates of OX7 in human, mouse and rat plasma.

1M disodium hydrogen phosphate buffer solution (125 µl, pH 7.19) and penicillin/streptomycin (6 µl, Flow Labs Cat. No. 16-700-49) was added to 500 µl samples of fresh plasma from human, mouse (nu nu) and rat (Sprague-Dawley) sources. The samples were then sterile-filtered (0.22 µl) and each treated with an equal volume of a sterile solution of Ig-Kemptide-$^{32}$-P (450 µl at 225 µg/ml and 200 mCi/mmole Ig prepared as described in Example 4 but at a lower specific activity). The mixtures were incubated at 37° C. and triplicate samples (20 µl) were taken at a range of time points over a 64 hour period. Acid precipitates were obtained, collected on glass fibre filters and counted but showed no loss of radioactivity during the course of the experiment.

EXAMPLE 8

Comparison of the affinities of the conjugate H17E2-Kemptide-$^{32}$P for LOVO cells and T47-D cells.

Solutions of H17E2-Kemptide-$^{32}$P conjugate (50 µl, prepared as described in Example 5) at a range of concentrations were added to aliquots of LOVO (a human colorectal cancer cell line which expresses alpha-placental alkaline phosphatase) or T47-D cells (a human breast cancer cell line that does not express the alkaline phosphatase) at 10 cells/ 450 µl medium and incubated at 37° C. for one hour. After washing the cells, the amounts of radioactivity retained were measured. With the LOVO cells, the binding ranged from 2.60% at 10 ng/500 µl to 0.36% at 500 ng/ 500 µl while there was no measurable binding to the T47-D cells (0.05%). The viability of the LOVO cells was reduced by 40–55% with 1–100 ng of conjugate/assay and by 75% at 500 ng/assay.

EXAMPLE 9

Synthesis of Foxtide I

Foxtide I (the octapeptide Lys. Tyr. Arg. Arg. Ala. Ser. Leu. Gly) was synthesised using the "Classical" SPPS Merrifield chemistry on an "Applied Biosystems 430A Peptide Synthesiser".

EXAMPLE 10

Synthesis of Foxtide II

Foxtide II (the decapeptide Cys. Arg. Arg. Lys. Ala. Ser. Gly. Pro. Pro. Vale) was synthesised using the "Classical" SPPS Merrifield chemistry on an "Applied Biosystems 430A Peptide Synthesiser".

EXAMPLE 11

Figure 2:
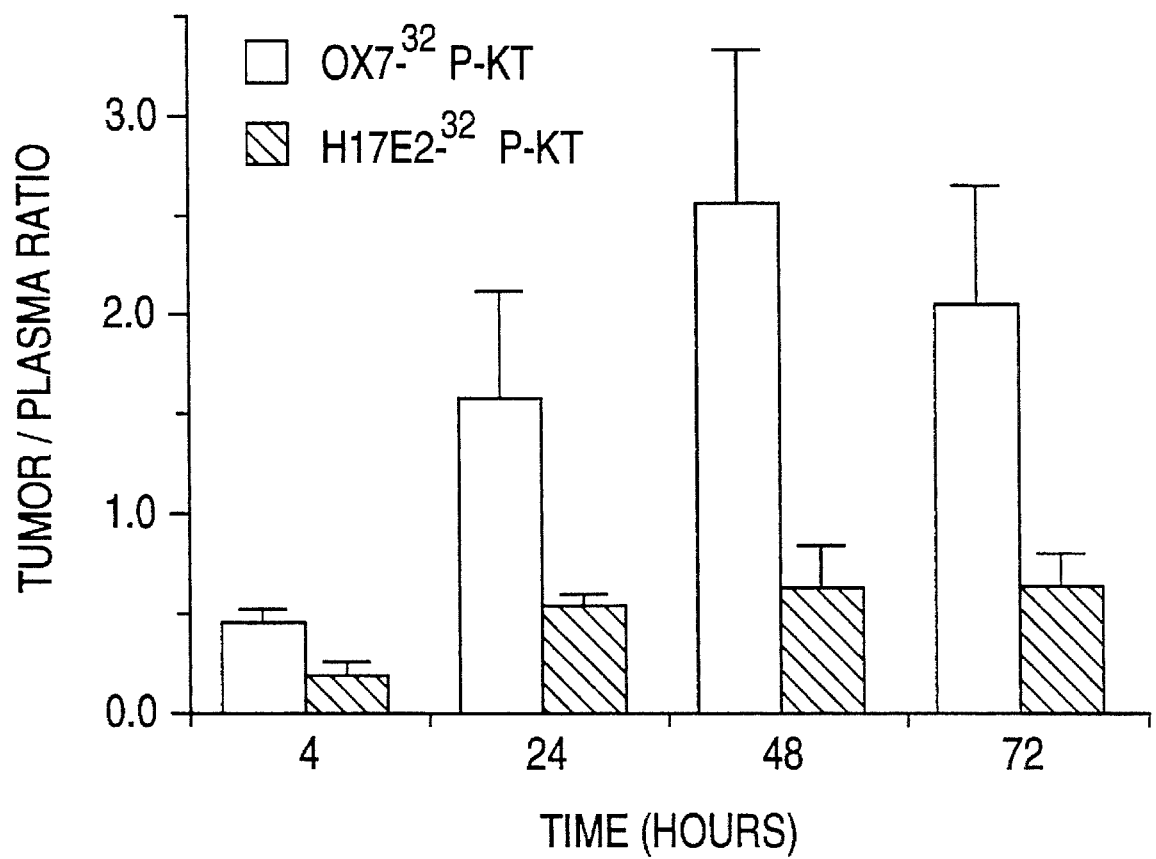
FIG. 2 is a graph illustrating clearance of the Kemptide conjugate as a function of time.

Localisation of OX7-Kemptide-$^{32}$P to subcutaneously implanted AKR A Lymphoma Solutions of either OX7-Kemptide-$^{32}$P conjugate (0.2 ml, 6.9 µCi) or H17E2-Kemptide-$^{32}$P conjugate (0.2 ml, 8.0 µCi) were injected intravenously into nu nu mice which had been previously implanted subcutaneously with AKR A lymphoma cells ($3 \times 10^6$ per mouse). The AKR A lymphoma has surface receptors which bind OX7 antibody. The mice were killed and blood samples taken following the removal of the tumours. Measurement of the radioactivity in the tissues (FIG. 1) showed that the maximum accumulation of the OX7-conjugate by the tumour occurred within 24 hours. This was followed by a steady loss of label from the tumour which dropped by half over the following 48 hour period. However, the OX7 conjugate clears from the bloodstream faster as the increasing plasma ratios indicate (FIG. 2). The apparent tumour uptake of the non-specific H17E2 conjugate is largely due to the blood circulating through the tumour.

We claim:

1. A method for modifying an antibody or an antigen binding fragment thereof which specifically binds to a tumor-associated antigen in order to facilitate labelling of said antibody or antigen binding fragment with $^{32}$P comprising covalently attaching to said antibody or fragment a peptide substrate for phosphokinase having up to about 20 amino acid residues wherein the covalent attachment of said peptide substrate does not affect the antigen-binding specificity of said antibody or antigen-binding fragment.

2. A method for modifying an antibody or an antigen binding fragment thereof which specifically binds to a tumor-associated antigen in order to facilitate labelling of said antibody or antigen binding fragment with $^{32}$P comprising covalently attaching to said antibody or fragment a peptide substrate for photophokinase having the amino acid sequence Leu Arg Arg Ala Ser Leu Gly wherein the covalent attachment of said peptide substrate does not affect the antigen-binding specificity of said antibody or antigen-binding fragment.

3. A method for modifying an antibody or an antigen binding fragment thereof which specifically binds to a tumor-associated antigen in order to facilitate labelling of said antibody or antigen binding fragment with $^{32}$P comprising covalently attaching to said antibody or fragment a peptide substrate for phosphokinase having the amino acid sequence Lys Tyr Arg Arg Ala Ser Leu Gly wherein the covalent attachment of said peptide substrate does not affect the antigen-binding specificity of said antibody or antigen-binding fragment.

4. A method for modifying an antibody or an antigen binding fragment thereof which specifically binds to a tumor-associated antigen in order to facilitate labelling of said antibody or antigen binding fragment with $^{32}$P comprising covalently attaching to said antibody or fragment a peptide substrate for phosphokinase having the amino acid sequence Cys Arg Arg Lys Ala Ser Gly Pro Pro Val wherein the covalent attachment of said peptide substrate does not affect the antigen-binding specificity of said antibody or antigen-binding fragment.

5. A peptide having the amino acid sequence Lys. Tyr. Arg. Arg. Ala. Ser. Leu. Gly.

6. A peptide having the amino acid sequence Cys. Arg. Arg. Lys. Ala. Ser. Gly. Pro. Pro. Val.

* * * * *